United States Patent [19]
Napierkowski et al.

[11] Patent Number: 5,239,781
[45] Date of Patent: Aug. 31, 1993

[54] REINFORCED CLOSURE FOR A PRESSURE VESSEL

[75] Inventors: Susan M. Napierkowski, Erie; E. L. Thomas, Jr., North East; Arthur T. Nagare, Erie, all of Pa.

[73] Assignee: American Sterilizer Company, Erie, Pa.

[21] Appl. No.: 861,727

[22] Filed: Apr. 1, 1992

[51] Int. Cl.⁵ .............................................. E06B 3/00
[52] U.S. Cl. ......................................... 49/501; 52/630
[58] Field of Search ................ 49/501, 404, 431, 502; 160/370.1; 52/630

[56] References Cited

U.S. PATENT DOCUMENTS

| | | | |
|---|---|---|---|
| 1,340,243 | 5/1920 | Oliver | 52/630 X |
| 1,450,255 | 4/1923 | Gilpin | 52/630 X |
| 3,478,916 | 11/1969 | Linder . | |
| 3,681,008 | 8/1972 | Black . | |
| 3,694,962 | 10/1972 | McDonald et al. . | |
| 4,228,135 | 10/1980 | Wolff . | |
| 4,335,075 | 6/1982 | Kackos . | |
| 4,543,748 | 10/1985 | North, Jr. . | |

OTHER PUBLICATIONS

Drawing of a standard flat plate door.
Drawing of a door on a sterilizer manufactured by Getinge International Inc. of Lakewood, N.J.

*Primary Examiner*—Philip C. Kannan
*Attorney, Agent, or Firm*—Jones, Day, Reavis & Pogue

[57] ABSTRACT

A closure for a pressure vessel of the type in which the pressure vessel door is preferably slidably attached to the pressure vessel by door retention assemblies. The door is constructed of a plate member to which bars are attached at opposing edges of the door. Slider portions are inset in a portion of the surface of each slider bar to enhance sliding contact with the door retention assemblies in sliding door embodiments of the invention. A plurality of reinforcing members span the plate member between slider bars and taper from a maximum elevation at or adjacent the center of the reinforcing member to a minimum elevation at the edges of the reinforcing member, where a flange sandwiches the slider bars between the plate member and the flange.

6 Claims, 2 Drawing Sheets

REINFORCED CLOSURE FOR A PRESSURE VESSEL

BACKGROUND OF THE INVENTION

1. Field of the Invention

The invention relates to sliding doors. More particularly, the invention relates to apparatus for reinforcing the sliding door of a pressure vessel.

2. Description of the Invention Background

Pressure vessels, such as industrial sterilizers and autoclaves, are well known in the art and are generally used in hospitals, industrial laboratories, and other facilities for the purpose of sterilizing various solid, porous, or liquid items.

Sliding doors are sometimes used in connection with such machines because they require a minimum of space in relation to the size of the opening they provide and they do not interfere with the loading and unloading of the machine. Sliding doors are held along opposing sides (vertical or horizontal, depending on the direction in which the door slides) by a retention system. The retention system of some conventional doors includes a rail or trough-like member in which the captive edge of the sliding door is received.

Because of the pressure forces which build up in pressure vessel chambers, sliding doors for these vessels must be generally designed to withstand large forces. Sliding pressure vessel doors, held captive on two sides, are subject to both a deflective and a stress force across the door surface. It has been observed that the forces acting on the door are relatively high at the door's center. Therefore, the cross-section of the door at its center must be sized to handle the increased forces in that area. Several conventional sliding doors use a flat plate door, uniform in cross-section. Others enhance the flat plate with reinforcing beams or channels.

The simplest conventional door design is one consisting of a thick metal plate, uniform in cross-section and machined for flatness. Manufacturing such a door does not involve welding, but is expensive and difficult because of the large mass of material required. The mill plate typically used does not have a flatness tolerance and, therefore, it is necessary to start with a thicker plate and machine it to the desired flatness and thickness. The flat plate must be thick enough to withstand the stresses at the door center. However, continuing this large cross-section out to the captive sliding edges of the door requires the use of a commensurately large width in the rail or trough of the door retention system. The width of the retention system is sometimes referred to as the gap. The larger gap in the door retention system required for a flat plate door in turn, provides a relatively long "tunnel" length for vessel loading and unloading from the interior to the exterior of the vessel.

One commercially available 26"×26" pressure vessel door includes horizontal, reinforcing channel beam members which are intermittently welded to the surface of a flat plate member. The channel beam members are uniform in cross-section and extend across the full width of the door. The edges of the door are welded to large stiffener bars which ride within the trough of the door retention assembly. The width of the trough is relatively large to accommodate the large stiffener bars. Because of the size of the stiffener bars, this door also provides a relatively long "tunnel" length or loading and unloading.

A commercially available 17"×18" door includes reinforcing beams in the form of bent angles in place of the channel beam members of the 26"×26" door. Each bent angle reinforcing beam is also uniform in dimension across its span. The 17"×18" door includes slider bars along both captive edges of the door. Each end of the bent angle reinforcing beams are joined to a stiffener bar. The slider bars which are received in the retention assembly, are not as thick as the stiffener bars of the 26"×26" door so that the width of the trough in the retention system of the 17"×18" door is smaller. However, this design requires a number of pieces and much welding. The bent angles do not reinforce the sliding surface or the engagement between the sliding surface with the door.

An additional concern which must be addressed in the design of sliding pressure vessel doors is that they include a properly supported sliding surface for door translation. The sliding surface must somehow be connected to the door edges such that the junction between the sliding surface and the door may withstand the high stress forces to which it is subjected.

It is therefore an object of the present invention to provide a pressure vessel closure and a means for reinforcing the closure that withstand the stress levels exerted across the door and at its edges while minimizing the width of the trough in the retention assemblies in which the door slides, thereby reducing "tunnel" length. The several different pressure vessel door designs which exist have not satisfactorily addressed these objectives.

SUMMARY OF THE INVENTION

In accordance with the present invention, there is provided an improved design for a pressure vessel closure. The apparatus of the present invention is particularly suited for use on pressure vessels wherein the door is slidably attached to the vessel.

The present invention includes apparatus for reinforcing a door or closure against which forces are exerted. The apparatus is comprised of a reinforcement member which has a first elevation at each end thereof and a second elevation, greater than the first elevation, intermediate the ends at a location, typically the center, generally where the forces exerted against the door are concentrated. The surface of the reinforcement member preferably tapers from the second elevation downwardly to the ends. Each end of the reinforcement member may be configured to define a flange overhanging a recess.

The vessel with which the present invention is used preferably includes retention means for retaining the closure. The retention means include opposing spacer members and retention members which together define a groove on each side of the opening of the vessel for slidably receiving a closure.

The closure of the present invention includes a plate member and a plurality of the reinforcing members. Means are provided to attach the closure to the surface of the vessel.

The attachment means may include two edge members mounted along opposing edges of the plate member. At least a portion of each edge member may be constructed for sliding contact within one of the opposing grooves of the retention means.

The reinforcing members preferably have a first surface rigidly connected in a confronting relationship to the plate member, spanning the plate member from one edge member to the other. The reinforcing members may be, for example, either solid, hollow or generally U-shaped channel beam members. The reinforcing members have a second surface which preferably tapers from a maximum elevation at or about the plate member's center where the stress force is maximized, to a minimum elevation at the edges of the plate member, where the flanged edge overlaps the edge members, thus allowing a relatively small cross-section of reinforcing member to sandwich the edge members against the plate member, while maintaining a small gap in the vessel's closure retention means. The overlapping flanges reinforce the engagement between the edge members and the plate member. The number of reinforcing members used, the dimensions of the reinforcing members at the center of the plate member, and the thickness of the plate member are determined as a function of the pressure expected to be present in the vessel, the dimensions of the vessel opening, and the materials used in constructing the closure.

Accordingly the present invention overcomes the disadvantages of the prior pressure vessel closure designs described above. The present invention provides for a reduced-weight pressure vessel closure which is designed to withstand the relatively great stress forces at the center of the closure, while providing a minimized overall cross-section at the sides of the door to reduce tunnel length. In addition, the present invention provides a means to reinforce the engagement between the edge members and the plate member of the closure.

BRIEF DESCRIPTION OF THE DRAWINGS

The preferred embodiment of the invention will now be described by way of example only, with reference to the accompanying Figures wherein like members bear like reference numerals.

DETAILED DESCRIPTION OF THE PREFERRED EMBODIMENT

Figure 2:
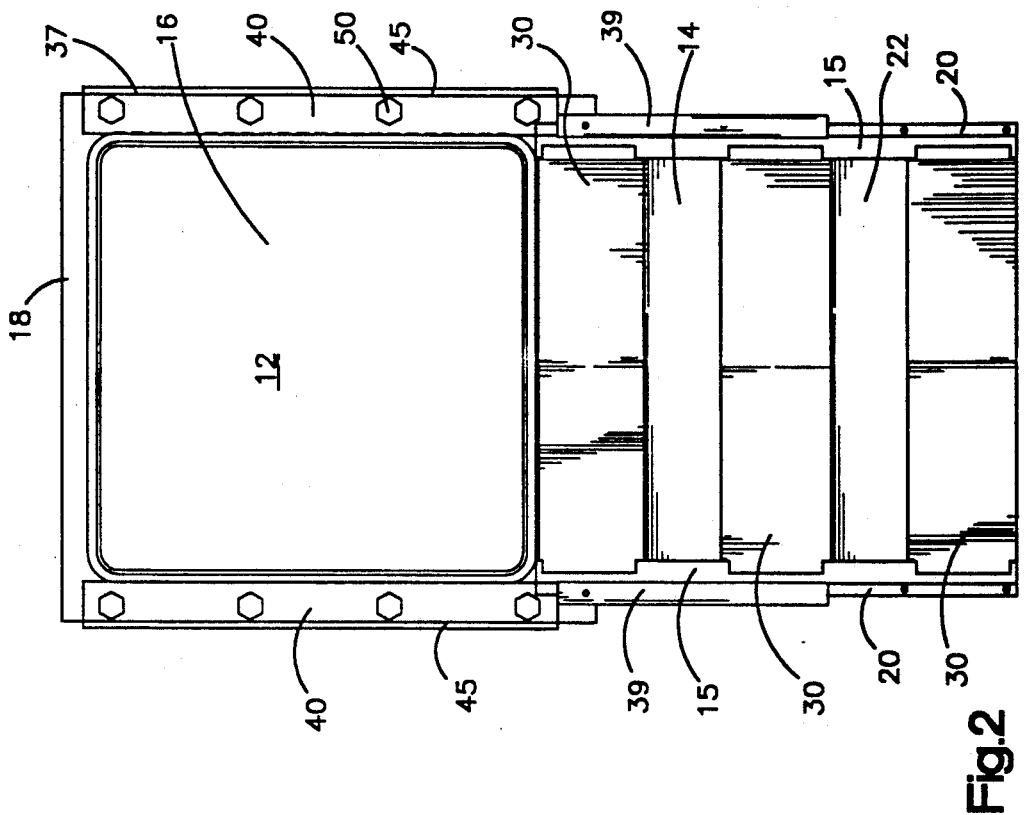
FIG. 2 is a front elevational view of a pressure vessel incorporating the preferred embodiment of the closure of the present invention wherein the door of the pressure vessel closure is in the fully open position.
Figure 1:
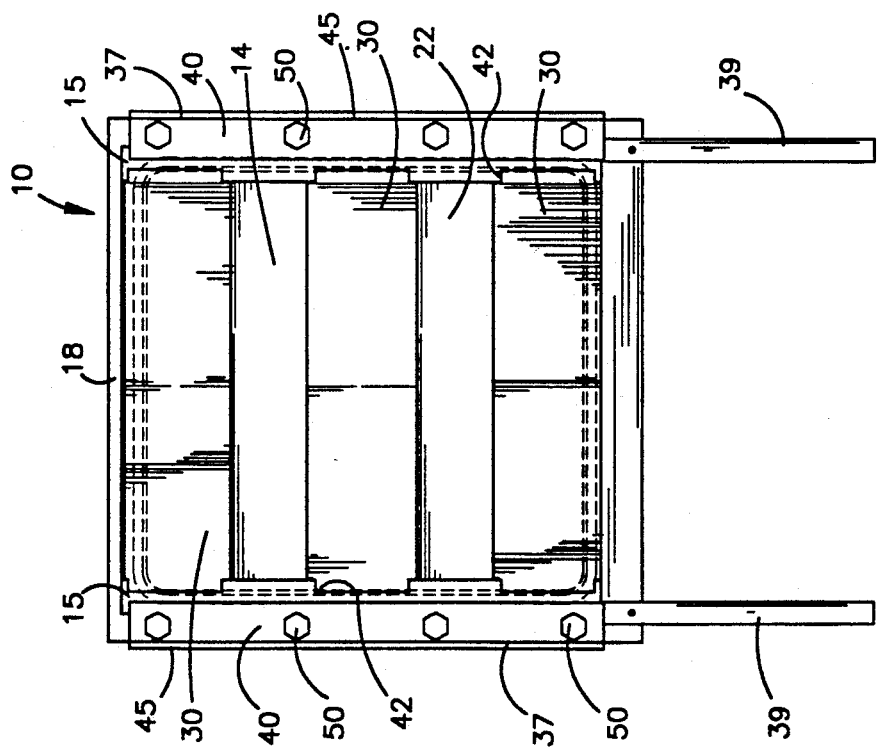
FIG. 1 is a front elevational view of a pressure vessel incorporating the preferred embodiment of the closure of the present invention wherein the door of the pressure vessel closure is in the fully closed position.

Referring now to the drawings which are for purposes of illustrating the preferred embodiment of the present invention only and not for purposes of limiting the same, FIGS. 1 and 2 show a sliding pressure vessel closure system 10 of the preferred design adapted to fit over the opening of a conventional pressure vessel 12. The pressure vessel 12 is typical of pressure vessels having sliding doors, the construction and operation of which are well known in the art. Because such vessel designs are well known in the art, a detailed description of the pressure vessel need not be set forth herein beyond what is necessary to understand the present invention.

As shown in FIG. I, the pressure vessel closure system 10 includes a sliding pressure vessel door 14 which, when in the fully closed position depicted, completely covers the pressure vessel opening 16. The sliding pressure vessel door 14 may be slid to the fully open position depicted in FIG. 2 such that the opening 16 is fully accessible. Although FIGS. 1 and 2 depict a pressure vessel door 14 which slides vertically downward to reveal the chamber opening 16, it is contemplated that the vessel closure system 10 of the present invention can be mounted for sliding in other directions to reveal a vessel's opening. It is further contemplated that the reinforcing members 30 on the door 14 may be used on non sliding doors.

A pair of oppositely placed door retention assemblies 37 are rigidly connected to the pressure vessel 12 by fastening means, for example, retention bolts 50. The pressure vessel door 14 is slidably retained to the pressure vessel 12 by door retention assemblies 37 which, in turn, are attached to the front wall 18 of the pressure vessel chamber 12. The door retention assemblies 37 maintain the position of the pressure vessel door 14 against the outward forces created during operation of the pressure vessel 12. The pressure vessel 12 also includes a pair of oppositely positioned lower guide members 39 which guide and retain the door 14 between the fully closed and the fully opened positions depicted in FIGS. 1 and 2, respectively.

Figure 4:
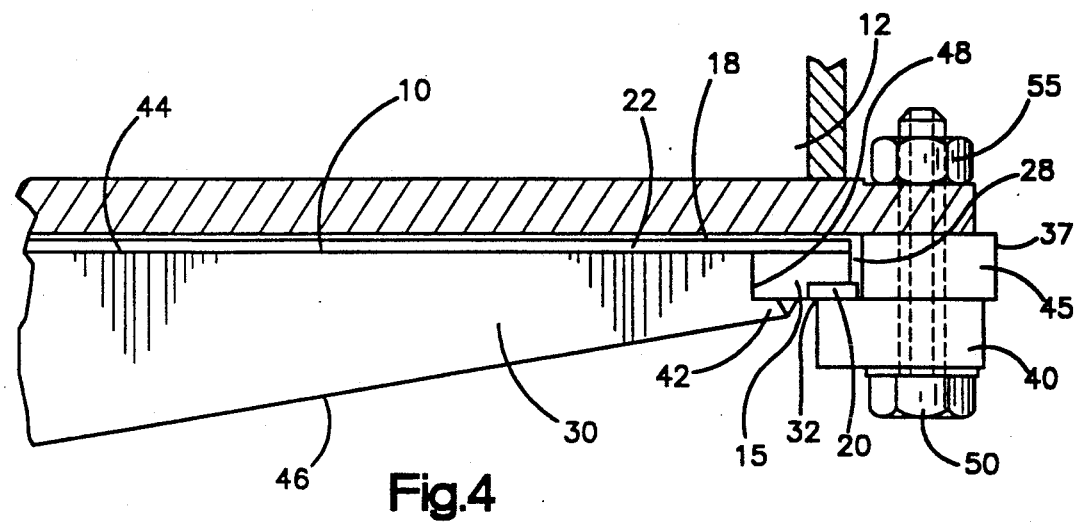
FIG. 4 is a top, partial sectional view of the closure and retention means of the pressure vessel of FIG. 1.

FIG. 4 depicts the components of door retention assemblies 37 in relation to the pressure vessel door 14. Each door retention assembly 37 includes a retention bar 40 spaced from the pressure vessel front wall 18 by a spacer member 45. In the embodiment shown, the retention bars 40 and the spacer members 45 are attached along opposing sides of the front wall 18 by retention bolts 50 which pass through the front wall 18 and are secured by nuts 55. Retention bar 40 extends beyond spacer member 45 to define a trough 28 between the interior face 32 of the retention bar 40 and the front wall 18 of the vessel 12 for receiving the sliding edge of the door 14. One preferred embodiment includes one inch thick spacer members 45, thus creating a one inch trough 28, or gap, in the door retention assemblies 37 to retain the pressure vessel door 14. The pressure vessel door 14 is held in place against the pressure vessel 12 such that the door may slidably move along the trough 28 against the interior face 32 of retention bar 40 of the retention assembly 37.

Figure 3:
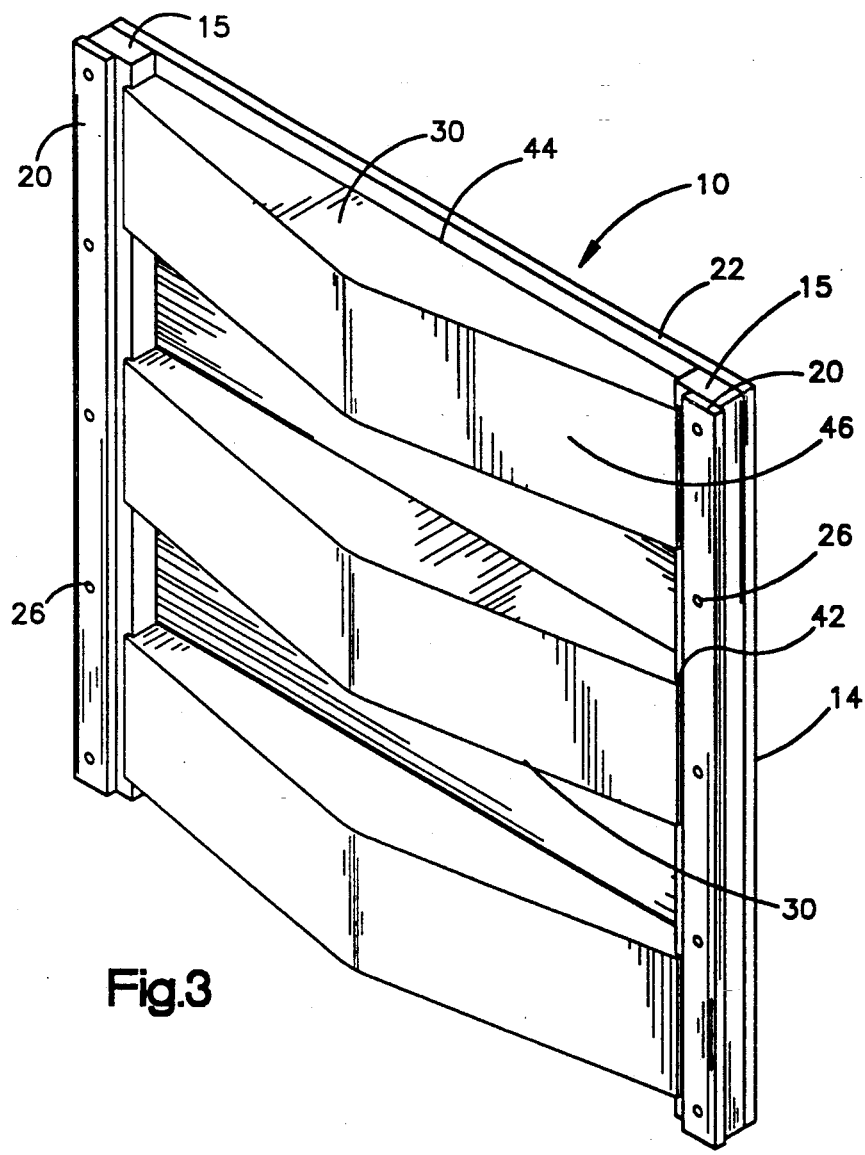
FIG. 3 is a perspective view of the preferred embodiment of the reinforced closure of the present invention.

The pressure vessel door 14 of the present invention, shown removed from the retention assemblies 37 in FIG. 3, is constructed from a flat, preferably stainless steel or nickel clad carbon steel, plate member 22. At least the opposing captive edges, and preferably all, of the plate member 22 are of a uniform thickness. Edge members, or slider bars, 15 are mounted along each opposing captive edge of the plate member. A plurality (three are shown) of reinforcing members 30 are provided to span the distance between the slider bars 15. At least a portion of each slider bar 15 is made of a material or constructed to enhance sliding contact with the interior face 32 of retention bar 40 in trough 28. In the preferred embodiment, a slider portion 20 is, either wholly or partially, inset in the slider bar 15 in confronting relationship with the interior face 32 of the retention bar 40. The slider portions 20 actually contact the interior face 32 of retention bars 40. It is therefore advantageous that the slider portion be constructed of a material which allows easy sliding movement of the door, such as, for example, brass, a teflon-coated material or highly polished surfaces.

In one embodiment of a 26"×26" pressure vessel closure system 10 made according to the present invention, the plate member 22 is preferably of a ¼ inch minimum thickness and the slider bars 15 are preferably ⅜ inch thick×1¼ inch wide. The slider bars 15 may be separate pieces, rigidly attached and preferably vertically welded at opposite ends of the plate member 22. Alternatively, the slider bars may be machined, integral portions of the door 14. The slider portion 20 is rigidly attached to each slider bar 15, preferably by countersunk screws 26.

The reinforcing members 30 have a first surface 44 in confronting relationship with the plate member 22. The first surface is preferably welded to the outer surface of the plate member 22. In the preferred embodiment, the reinforcing members used are hollow and formed from ¼ inch thick metal. They have a second, outer surface 46 constructed to withstand the pressure exerted against the plate member 22. Because the pressure force on the pressure vessel door is at a maximum or concentrated at about the door's center, the second surface 46 of the reinforcing members 30 provided by the present invention have an elevated section, generally in the location (typically the center) where the forces exerted against the door are concentrated intermediate the ends adjacent the edges of the pressure vessel door 14. The number of reinforcing members 30 used, as well as the dimensions of the members 30 themselves and location at about the center and the thickness of the plate member 22, are determined as a function of the pressure levels expected to be used in a particular vessel, the dimensions of the vessel opening, and the materials used in constructing the door components.

As shown in FIG. 4, each reinforcing member 30 tapers from its elevated intermediate, preferably central, position to an area of a lower elevation at each end which defines a flanged portion 42 and a recessed portion 48. The flanged portion 42 on each edge of the reinforcing member 30 overlaps one edge of the slider bar 15, but does not overlap the slider portion 20. The slider bar 15 is seated in the recess 48 between the flanged portion 42 and the plate member 22. This overlapping design overcomes a disadvantage of the prior designs in that the overlap reinforces the engagement between the plate member 22 and the slider bar 15 and distributes the stresses from the reinforcing members 30 to the slider bar 15. Other suitable configurations which will similarly reinforce the engagement may be used.

The present invention's preferred design, whereby the reinforcing members 30 taper downwardly and outwardly from their centers, allows a reinforced door for a pressure vessel 12 which will withstand the forces acting on the door, but which has a reduced overall cross-sectional area at the door's captive, sliding edges. This novel design minimizes the gap between the interior face 32 of the retention bar 40 and the front wall 18 of the pressure vessel 12 without hinderance of the sliding motion of the door 14 and, importantly, without sacrificing reinforcing strength. Reduction of this gap reduces the length of the "tunnel" through which items must be passed through to the pressure vessel 12.

As such, the present invention, as described hereinabove, addresses the various problems encountered when using existing pressure vessel closure designs. However, it will be appreciated that various changes in details, materials and arrangements of parts which have been herein described and illustrated in order to explain the nature of the invention, may be made by those skilled in the art within the principle and scope of the invention as expressed in the appended claims.

What is claimed is:

1. Apparatus for reinforcing a door against forces exerted against the door comprising:
   a reinforcement member for spanning the door and having a first elevation at each end thereof and a second elevation, greater than the first elevation intermediate the ends at a location generally where the forces exerted against the door are concentrated;
   wherein the door is for use with a vessel and further comprising means joined to each end of the reinforcement member for slidably mounting the door on the vessel; and
   wherein each end of the reinforcement member is configured to define a flange overhanging a recess.

2. The apparatus recited in claim 1 wherein the means for slidably mounting the door is positioned within the recess on each end of the reinforcement member and the flange reinforces the engagement between the door and the means for slidably mounting the door.

3. A closure for a vessel comprising:
   a plate member;
   a plurality of reinforcing member spanning the plate member, each reinforcing member having opposing ends of a minor elevation and a portion intermediate the opposing ends of a major elevation;
   means for attaching the closure to the vessel; wherein the vessel includes retention members and spacer members on opposing sides of an opening in the vessel defining opposing grooves on each side of the opening for slidably receiving a closure and the means for attaching the closure to the vessel comprises two slide bars mounted on opposing edges of the plate member for sliding engagement within the opposing grooves.

4. The closure recited in claim 3 wherein each end of each reinforcing member is configured for engagement with a complementary surface on the slide bars for reinforcing the contact between the plate member and the slide bars.

5. The closure recited in claim 4 wherein each end of each reinforcing member defines a recess having an overhanging flange and each slide bar has an edge portion which sits in the recesses of the ends of the reinforcing members.

6. A closure for a pressure vessel which includes opposing retention means for retaining the closure and wherein pressure forces are exerted comprising:
   a plate member having opposing edges of generally a uniform thickness;
   two edge members, one edge member being mounted along each opposing edge of the plate member and at least a portion of each edge member being constructed for sliding contact with one of the opposing retention means;
   a plurality of reinforcing members for reinforcing the plate member against pressure forces exerted against the plate member within the pressure vessel, each reinforcing member spanning the plate member between the opposing edge members and having a first surface in confronting relationship with the plate member, a second surface and opposing ends, each opposing end being configured for reinforcing engagement with one of the opposing edge members, and the second surface of each reinforcing member having an elevated section intermediate and tapering toward each opposing end, the elevated section being positioned generally adjacent the portion of the plate member against which the pressure forces within the pressure vessel are concentrated.

* * * * *